United States Patent
Cho (10) Patent No.: US 8,816,286 B2
(45) Date of Patent: Aug. 26, 2014

(54) OPTICAL SIMULATION-BASED TIME-OF-FLIGHT COMPENSATION AND PET SYSTEM CONFIGURATION

(75) Inventor: Sanghee Cho, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 464 days.

(21) Appl. No.: 13/360,913

(22) Filed: Jan. 30, 2012

(65) Prior Publication Data

US 2013/0032706 A1 Feb. 7, 2013

Related U.S. Application Data

(60) Provisional application No. 61/513,717, filed on Aug. 1, 2011.

(51) Int. Cl.
| | |
|---|---|
| *G01T 1/16* | (2006.01) |
| *G01T 1/164* | (2006.01) |
| *G06T 7/00* | (2006.01) |
| *G01T 1/29* | (2006.01) |

(52) U.S. Cl.
CPC ............. *G01T 1/1647* (2013.01); *G06T 7/0012* (2013.01); *G01T 1/2985* (2013.01)
USPC .................................................. 250/363.03

(58) Field of Classification Search
CPC ................................ G01T 1/16; G06T 7/0012
USPC ....................................... 250/363.03; 382/131
See application file for complete search history.

(56) References Cited

U.S. PATENT DOCUMENTS

| | | |
|---|---|---|
| 2009/0032717 A1 | 2/2009 | Aykac et al. |
| 2010/0084560 A1 | 4/2010 | Aykac et al. |
| 2010/0098312 A1 | 4/2010 | Leahy et al. |
| 2011/0155898 A1 | 6/2011 | Burr et al. |
| 2011/0192982 A1 | 8/2011 | Henseler et al. |

OTHER PUBLICATIONS

Moses et al. "Prospects for Time-of-Flight PET Using LSO Scintillator". IEEE Trans. Nucl. Sci. 46 (3), Jun. 1999: p. 474-478.*
W. W. Moses and S. E. Derenzo "Prospects for time-of-flight PET using LSO scintillator", IEEE Trans. Nucl. Sci., vol. 46, pp. 474-478, 1999.
K. C. Burr, A. Ivan., D. E. Castleberry, R. A. Thompson, J. W. LeBlanc, K. Shah and R. Farrell, "Depth-of-interaction-encoding high-resolution PET detector with sub-nanosecond timing", IEEE Nuclear Science Symposium Conf. Rec., vol. 6, pp. 3880-3884, 2004.

(Continued)

*Primary Examiner* — Casey Bryant
(74) *Attorney, Agent, or Firm* — Peter L Kendall (57) ABSTRACT

A method of configuring a time-of-flight positron emission tomography (PET) system includes determining a set of parameters of a detector of the PET system. Each parameter is configured to affect photon travel within the detector. The method further includes simulating operation of the detector to generate a photon detection timing data profile for a plurality of depth of interaction (DOI) positions within the detector via a simulation model of the detector configured in accordance with the set of parameters, and determining a time-of-flight correction factor for each DOI position of the plurality of DOI positions based on the simulated operation. The correction factor is indicative of a time offset of the photon detection timing data profile.

20 Claims, 5 Drawing Sheets

(56) References Cited

OTHER PUBLICATIONS

F. Bauer, J. Corbeil, M. Schmand and D. Henseler, "Measurements and ray-tracing simulations of light spread in LSO crystals", IEEE Trans. Nucl. Sci., vol. 56, pp. 2566-2573, 2009.

D. Henseler, R. Grazioso, N. Zhang and Matthias Schmand, "SiPM performance in PET applications: An experimental and theoretical analysis," IEEE Nuclear Science Symposium Conf. Rec., N28-1, pp. 1941-1948 (2009).

L. G. Hyman, "Time resolution of photomultiplier systems,", Rev. Sci. Instr., vol. 36, No. 2, pp. 193-196, 1965.

Y. Shao, "A new timing model for calculating the intrinsic timing resolution of a scintillator detector,", Phy. Med. Biol., vol. 52, pp. 1103-1117, 2007.

Shibuya et al., "Timing resolution improved by DOI information in an LYSO TOF-PET detector", IEEE Nuclear Science Symposium Conference Record, pp. 3678-3680 (2007).

Wiener et al., "Signal analysis for improved timing resolution with scintillation detectors for TOF PET imaging", IEEE Nuclear Science Symposium Conference Record, 5 sheets (2010).

Spanoudaki et al., "Investigating the temporal resolution limits of scintillation detection from pixelated elements: comparison between experiment and simulation", Phys. Med. Biol. 56, pp. 735-756 (2011).

Conti, "State of the art and challenges of time-of-flight PET", Physica Medica 25, pp. 1-11 (2009).

* cited by examiner

OPTICAL SIMULATION-BASED TIME-OF-FLIGHT COMPENSATION AND PET SYSTEM CONFIGURATION

CROSS-REFERENCE TO RELATED APPLICATION

This application claims the benefit of U.S. provisional application entitled "Utilizing the Depth-of-Interaction (DOI) Information to Improve the Timing Resolution on Time-of-Flight PET Systems," filed Aug. 1, 2011, and assigned Ser. No. 61/513,717, the entire disclosure of which is hereby incorporated by reference.

BACKGROUND

The present embodiments relate to time-of-flight (TOF) positron emission tomography (PET).

Nuclear medicine uses radiation emission to acquire images that show the function and physiology of organs, bones or tissues of the body. Radiopharmaceuticals are introduced into the body by injection or ingestion. These radiopharmaceuticals are attracted to specific organs, bones, or tissues of interest. The radiopharmaceuticals cause gamma photons to emanate from the body, which are then captured by a detector. The interaction of the gamma photons with a scintillation crystal of the detector produces a flash of light. The light is detected by an array of optical sensors of the detector.

Positron emission tomography (PET) is a nuclear medicine imaging technique that uses a positron emitting radionuclide. PET is based on coincidence detection of two gamma photons produced from positron-electron annihilation. The two gamma photons travel in opposite directions from the annihilation site, and can be detected by two opposing detectors of a ring of detectors. Annihilation events are typically identified by a time coincidence in the detection of the two gamma photons. The opposing detectors identify a line-of-response (LOR) along which the annihilation event occurred.

The quality of PET images is improved when the timing resolution supports a comparison of the arrival times of the two gamma photons. Some PET systems use the comparison to determine the time of flight of each gamma photon from the annihilation site. So called time-of-flight PET system use the time-of-flight information to determine where along the line of response the annihilation occurred. The annihilation site is thus located more accurately, improving the PET image.

BRIEF SUMMARY

By way of introduction, the preferred embodiments described below include methods and systems for configuring a time-of-flight positron emission tomography (PET) system, and/or compensating time-of-flight information in a time-of-flight PET system. An optical simulation is used to determine correction factors for varying depths of interaction within a PET detector. Compensation of the time-of-flight data based on the correction factors may improve image quality.

In a first aspect, a method is provided for configuring a PET system, in which photon travel within a detector of the PET system is simulated with a processor via an optical simulation model of the detector. A photon timing profile is generated via the simulated photon travel for a plurality of depth of interaction (DOI) positions within the detector. A time-of-flight correction factor is determined for each DOI position of the plurality of DOI positions based on the simulated photon travel. The correction factor is indicative of a respective time offset of each photon timing profile. The time-of-flight PET system is configured to determine time-of-flight values in accordance with the time-of-flight correction factors.

In a second aspect, a PET system includes a detector having a scintillation crystal and an optical sensor in optical communication with the scintillation crystal, the optical sensor being configured to capture photons generated in the scintillation crystal at a plurality of depths of interaction. The PET system further includes a memory in which time-of-flight correction data is stored, the time-of-flight correction data being indicative of timing offset simulation data based on an optical simulation model, the optical simulation model being configured in accordance with a set of parameters to simulate photon travel within the detector from each depth of interaction of the plurality of depths of interaction. The set of parameters include a parameter representative of the scintillation crystal. The PET system further includes a processor in communication with the memory and the detector to compensate time-of-flight data based on interaction depth data and the time-of-flight correction data.

In a third aspect, a method of positron emission tomography (PET) includes receiving data indicative of a depth of a gamma interaction at which photons are generated for detection by a PET detector, and correcting, with a processor, a time of flight for the gamma interaction based on the depth and based on photon detection timing profile offset data, the photon detection timing profile offset data being based on a simulation of operation of the PET detector at a plurality of depths of interaction. The simulation is based on an optical model of the PET detector, the optical model being configured in accordance with a plurality of parameters of the PET detector. The method further includes reconstructing an image based on the corrected time of flight. The plurality of parameters may include scintillation crystal geometry parameters representative of a scintillation crystal of the PET detector.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

PET systems, as well as systems and methods for configuring PET systems, are described. The methods and systems may improve timing resolution in time-of-flight PET based on information indicative of the depth at which a gamma photon interacts with a PET detector. The depth of interaction may be used to determine a correction or compensation factor that reduces timing jitter otherwise present in time-of-flight data. The timing jitter may be introduced by variance in the duration of time between the interaction and detection by a photosensor or other optical sensor of the PET detector. Such time variance may result from varying photon travel paths (and, thus, lengths) between the interaction and the optical sensor.

The variance in photon travel may be substantial due to the elongated nature of scintillator crystals in PET detectors. Each scintillator crystal is often elongated for high efficiency in converting gamma photons into visible photons. Increasing the length of the scintillator crystals, in turn, increases the likelihood of gamma photon interaction and, thus, detection. Gamma interaction may nonetheless still occur anywhere in the scintillation crystal. The elongated crystal geometry allows variation in the depth of interaction of the gamma photons. Thus, the visible photons produced by interactions at depths significantly spaced from the optical sensor are more likely to undergo a greater number of reflections before reaching an optical sensor of the PET detector. In some cases, the photons may be reflected back and forth many times within the PET detector before detection by the optical sensor. In other cases, the photons may be reflected fewer times. The resulting indirect travel paths lead to non-negligible variance in photon arrival times. Further timing variance may be introduced by the difference in speed between the gamma photons (e.g., the speed of light) and light photons in the scintillator material (e.g., roughly half of the speed of light, and material dependent). These and other sources of photon travel variance, resulting in timing jitter, may degrade the timing resolution in time-of-flight PET systems.

The PET system may compensate for timing jitter via an optical simulation of the PET detector. The optical simulation is used to quantify the photon arrival time dispersion as a function of depth of interaction position. The dispersion may be quantified as a misalignment or offset between timing datasets generated via the optical simulation. The offsets may then be used as a correction or compensation factor for adjusting the time-of-flight data.

The optical simulation may be based on a model of the PET detector. The model may be configured in accordance with a plurality of parameters that affect photon travel within the PET detector. For example, the model may be configured in accordance with characteristics of the scintillation crystal, the optical sensor, one or more reflectors, and other elements of the PET detector. The model may thus be adapted to various PET detector types, designs, etc. The disclosed methods and systems are thus not limited to any particular PET detector design, configuration, or arrangement.

The disclosed methods and systems may be used in connection with various types of PET systems. For example, the disclosed methods and systems may be used in any application where scintillation materials are used for high energy matter detection and accurate time-of-flight information is used. In non-time-of-flight PET systems, the disclosed methods and systems may be used to reduce the coincidence window to include fewer random events.

Figure 1:
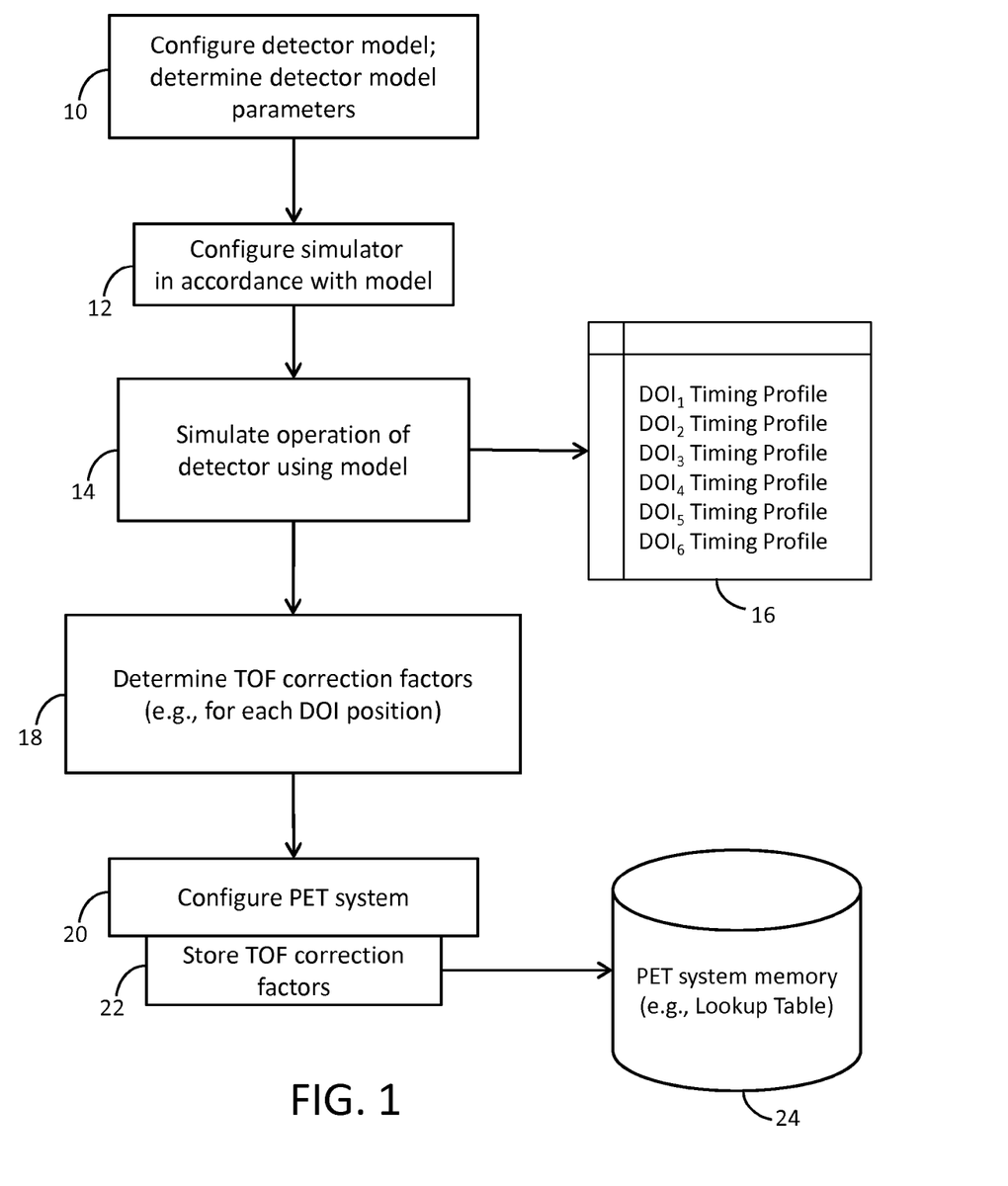
FIG. 1 is a flow diagram of one embodiment of a method for configuring a PET system.

FIG. 1 shows one embodiment of a method for configuring a time-of-flight PET system. The method may begin in act 10 in which a model of a PET detector of a PET system is constructed and/or configured. The PET detector model may include, or be configured via, a set of parameters. Each parameter may be incorporated into the PET detector model to represent one or more characteristics of the PET detector that affect, either directly or indirectly, photon travel within the PET detector. In some cases, a framework of the PET detector model is predetermined, in which case values for the set of parameters are provided to customize or otherwise configure the PET detector model for a specific PET system. In other cases, act 10 includes constructing the framework of the PET detector model by determining or modifying the characteristics of the PET detector to be modeled or represented and, thus, determining the parameters to be incorporated into the model.

The number, nature, and other aspects of the model parameters may vary. For example, the parameters may be directed to modeling one or more components of the PET detector, including, for instance, scintillation crystals, optical sensors, reflectors, sensor covers, coupling films, and packaging, as well as various components or aspects thereof (e.g., dimensions, shapes, ends or other surfaces, arrangements, refractive index, etc.). In some cases, one or more of the parameters may be directed to representing geometric characteristics of one or more scintillation crystals of the PET detector, such as its dimensions (e.g., length) and shape. Other characteristics of the scintillation crystals may also be represented, including, for instance, the material, positioning, the refractive index, the surface finish of one or more surfaces of the crystals (e.g., front end, back end, lateral sides), etc.

One or more parameters may be directed to representing an arrangement and other characteristics of the optical sensors adjacent the scintillation crystals, including the number, positioning, thickness, material, type, coupling film, etc., of the optical sensors. For example, the PET detector may include four optical sensors arranged in a two-by-two array. One or more parameters may be directed to representing a reflector arrangement of the PET detector. One or more components of the reflector arrangement may be considered part of the scintillation crystals. For example, each reflector may be formed along a side face of one of the scintillation crystals via the orientation of the cut that formed or shaped the crystal.

The PET detector model may be configured in accordance with theoretical aspects of the operation of the scintillator crystal. For example, one theoretical aspect may be directed to predicting or otherwise simulating the creation of visible photons arising from interactions with a gamma photon. The theoretical model may support the representation of various aspects of the visible photons, including, for instance, the direction of photon travel (considering, e.g., photon scattering), bulk absorption, photon speed, the number of photons generated, etc.

The optical simulation model of the PET detector may be configured in accordance with any combination of the aforementioned aspects or characteristics of the PET detector. Additional, fewer, or different parameters may be used. The optical simulation model may be constructed as an optical system configured in accordance with the parameters. The optical system may include any number of components (e.g., reflectors, regions of varying refractive index, reflectivity, transmittance and absorption, etc.) configured in accordance with one or more of the parameters.

The method may include configuring an optical simulator, or optical simulation system, in act 12 in accordance with the set of parameters of the optical simulation model. The optical simulator may be configured during, as part of, in parallel with, or after the implementation of act 10. The optical simulator may include a commercially available simulator, such as the ZEMAX optical system design simulator (Radiant ZEMAX LLC, Bellevue, Wash.), and/or other available simulators, such as the Monte Carlo simulator, DETECT2000, for design of photon sensing devices. The optical simulator may include one or more computers or other processors for implementing the simulations. Further details regarding exemplary systems for implementing the optical simulator are set forth below.

Initial conditions for the optical simulator may be set in accordance with one or more theoretical aspects of the PET detector model. For example, one or more initial conditions may reflect the number and nature of visible photons created by gamma photons as predicted by the theoretical model of the scintillation crystal.

The configuration of the optical simulator may be implemented as part of, or during, the construction of the model. The order of acts 10 and 12 may vary from the example shown in FIG. 1. For example, one or more aspects of the optical simulator may be configured before all parameters, or parameter values, of the PET detector model are completely established or set.

Figure 2:
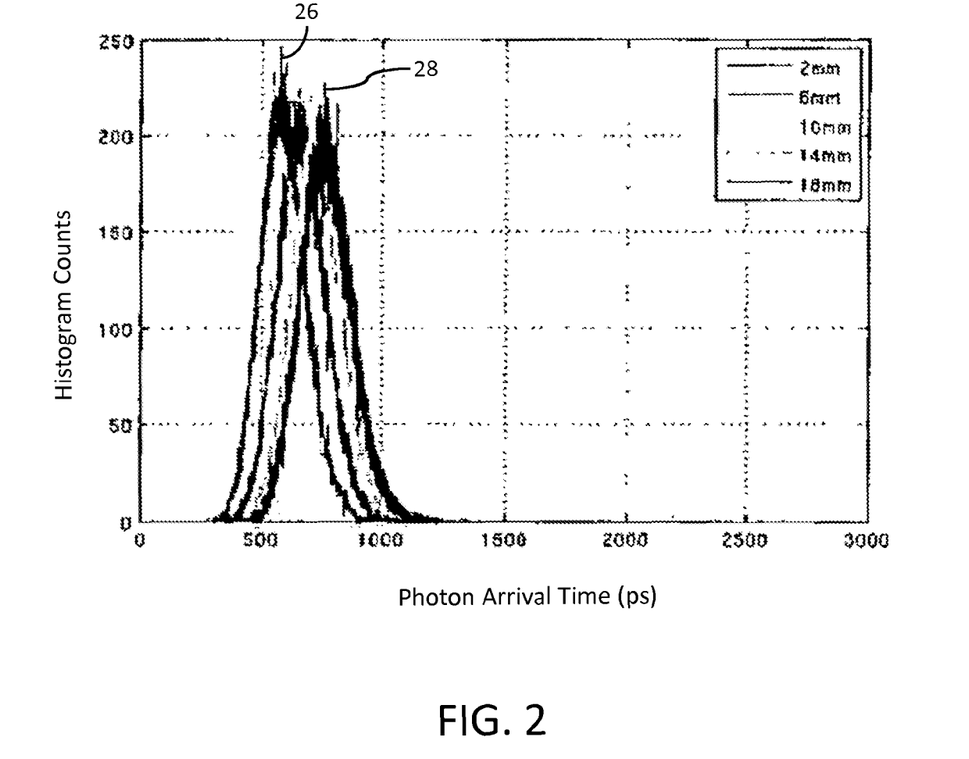
FIG. 2 is a graphical plot of photon arrival time profiles depicting variance or dispersion of photon arrival times in an optical simulation of a PET detector for a set of depth of interaction positions within the PET detector.

Once the optical simulator is customized to model the PET detector, the optical simulation is implemented in act 14. The optical simulator is used to simulate operation of the PET detector using the configured optical simulator. The simulated operation includes simulating the travel of the visible photons within the PET detector from a plurality of depths of interaction (e.g., $DOI_1$-$DOI_6$). The simulated travel begins in a scintillation crystal at a respective one of the interaction depths and ends at an optical sensor of the PET detector. The simulated travel is used to specify a distribution of travel times for the visible photons. The travel times are indicative of the times at which the visible photons arrive at the optical sensor of the PET detector. The distribution of arrival times generates a photon timing profile for each depth of interaction. Examples of photon timing profiles for a plurality of interaction depths are shown in FIG. 2, and described further below.

Data indicative of the photon timing profiles for the plurality of interaction depths may be stored in a data store 16 or other memory of the optical simulation system. In one example, the database may include a respective dataset for each photon timing profile (e.g., $DOI_1$ Timing Profile, $DOI_2$ Timing Profile, . . . , $DOI_n$ Timing Profile). Each dataset may include data indicative of the number of simulations in which a photon arrival time fell within an arrival time range or at a certain arrival time. The photon timing profiles need not be stored as separate datasets. In some embodiments, the photon timing profiles may be represented by, and stored as, fitted curves or other expressions of the arrival times. For example, each profile may be represented by a mean arrival time and standard deviation. The nature of the curve or other representation may vary. Not all profiles need to be represented in the same manner. The representation may thus vary from profile to profile. The nature of the representation may be determined in accordance with a functional or other analysis of the underlying simulation data.

The number of timing profiles in the data store 16 may vary. The spacing between the respective interaction depths for which timing profiles are generated may thus vary.

In act 18, time-of-flight correction factors are determined for each DOI position based on the results of the simulated photon travel. Each correction factor is indicative of an offset in arrival time for photons traveling from a respective depth of interaction. The arrival time offset is presented by the timing profile for the respective depth of interaction. The arrival time offset may be determined relative to the arrival time data for a reference dataset associated with, for instance, the shallow-most depth of interaction. In one embodiment, the correction factor determination includes comparing the timing profile for one of the interaction depths with the timing profile of the shallow-most depth of interaction, or other baseline timing profile. For example, the correction factor may be equal to, or otherwise derived from, the shift or other offset between the two timing profiles.

In some embodiments, a time difference between the two timing profiles is determined by the comparison. The arrival time data or other representation (e.g., a fitted curve) of the timing profiles may be processed in a variety of ways to determine the time difference, shift, or offset between two profiles. In one example, the timing profiles are analyzed to determine respective centers or peaks of the profiles, and the time difference between the two peaks is determined, and taken as the offset. The time-of-flight correction factor may then equal the offset, or be otherwise derived therefrom. Alternatively or additionally, the time difference may be determined by comparing other ranges, points, or other portions of the profiles. For example, the time difference may be a composite time difference between the profiles based on a number of points along the profiles (e.g., full width at half maximum, or FWHM) in addition or alternative to the profile peaks.

A PET system is configured in act 20 in accordance with the time-of-flight correction factors or any data representative thereof. In some embodiments, the data used to configure the PET system is processed by the PET system to determine the time-of-flight correction factor. In the example shown in FIG. 1, the correction factors are stored in act 22 in a PET system memory, such as a lookup table 24 or other database. A processor of the PET system involved in determining time-of-flight data for an event is communicatively coupled to the lookup table 24 or other memory to access the correction factors and adjust the time-of-flight data based on the correction factors and the depth of interaction in the PET detector. The time-of-flight data may thus be compensated for the effects arising from varying interaction depths.

The above-described methods may be implemented using the system(s) described below in connection with FIG. 3, or one or more other systems or computers, which may be coupled to, in communication with, or part of the time-of-flight PET system. The method is performed in the order shown, but other orders may be used. For example, one or more acts of the method may be implemented in a recursive or parallel manner. Additional, different, or fewer acts may be implemented. For example, the method may not include act 10 in embodiments in which the parameter set is predetermined. In another example, the method may include additional data processing acts to support additional or alternative analysis or processing, such as curve fitting, smoothing, extrapolation, etc., of the simulation data.

FIG. 2 depicts an example of the simulation data generated by implementing the optical simulation in accordance with the model of the PET detector. The simulation data is presented as a histogram of photon arrivals (or counts) as a function of photon arrival time for a number of depths of interaction. The depths are measured as a distance from the optical sensor. As a result, a timing profile 26 for the 2 mm interaction depth has the earliest photon arrival time peak compared to the other cases where the depth of interaction is farther away from the optical sensor. In some cases, the 2 mm interaction depth may be closer to the optical sensor, but farthest away from the patient, due to the scintillation crystals being disposed between the patient and the optical sensor in the PET scanner gantry. Timing profiles are depicted for interaction depths ranging from 2 mm to 18 mm, with a timing profile for every 4 mm increment.

The timing profile for each depth of interaction exhibits a distribution of photon arrival times. The distribution may have a Gaussian or near-Gaussian (e.g., parabolic-like) shape, which may follow from the random nature of the travel path of the visible photons between the interaction depth and the optical sensor. Each profile may be characterized by a peak or center arrival time at which the greatest number of photons arrive at the optical sensor. Each profile may be additionally or alternatively characterized by a mean or median arrival time, a standard deviation, or other statistical or data processing measure of variability. Each profile may be characterized by any number of aspects of the data distribution of the timing profile.

When viewed relative to the profile 26 for the 2 mm interaction depth, the distribution profiles for the other interaction depths are offset to the right due to later arrival times. The later arrival times arise from the longer path lengths (e.g., on average) traveled by the visible photons as the depth of interaction increases and, thus, the distance to the optical sensor increases. The profile 26 may be considered to be a baseline profile relative to which a timing offset for each other profile is determined. The offset may be determined in some embodiments by comparing the center or peak point of a profile for a respective interaction depth with the center or peak point of the baseline profile. Using the center-based comparison in this example, the timing offset of a timing profile 28 for an interaction depth of 18 mm is approximately 200 ps.

In alternative embodiments, other datasets may be used as the baseline profile. For example, the baseline profile may correspond with a theoretical travel path directly from a shallow interaction depth (e.g., 2 mm) to the optical sensor. The center or peak point of the theoretical travel path may then be equal to the travel time of the visible photon in the scintillation crystal along that direct path. A profile for a middle depth or other depth more likely associated with more actual events may be used as the reference. Regardless of the data used for the baseline profile, the compensation factors for various DOI locations may be determined relative thereto based on the profile distances shown in FIG. 2.

The disclosed methods and systems address the timing jitter, or timing dispersion, arising from the offsets between the timing profiles shown in FIG. 2. The disclosed methods and systems may shift the arrival times determined during operation by a time period corresponding with the timing offset shown in FIG. 2. Such time shifts may reduce the dispersion and, thus, timing jitter in time-of-flight PET systems.

In this example, optical simulation data is generated for interaction depths of 2 mm, 6 mm, 10 mm, 14 mm, and 18 mm. The set of interaction depths may vary. Optical simulation data may be obtained for any number of interaction depths. The resolution of the optical simulation data may thus vary, and may differ widely from 4 mm. Alternatively or additionally, the disclosed methods and systems may extrapolate from the optical simulation data to determine a timing profile for a depth of interaction not simulated (e.g., an interaction depth of 3 mm in the depicted example).

The simulation results reflect that the sensor is positioned on an outer end of the PET detector. The gamma radiation interacts with the scintillation crystal to convert the high-energy photon into visible light photons, which are detected by the sensor at the back of the crystal. However, the disclosed methods and systems may be used in connection with systems having sensors disposed at both ends of the crystal. The disclosed methods and systems are well suited for use with systems in which the DOI location is determined by measuring the light difference between the two sensors, and/or by calculating a timing difference.

The optical simulation may be configured in accordance with a fixed threshold triggering scheme. For example, photon arrivals are considered to be indicative of a gamma interaction once ten photons are captured by the optical sensor. Additional or alternative triggering schemes may be used. In some cases, the use of a different triggering scheme may involve a conversion of the triggering level of the triggering scheme to the fixed threshold triggering scheme of the optical simulation. The conversion may thus be used to calculate the corresponding number of photons to be captured for each gamma interaction.

Figure 3:
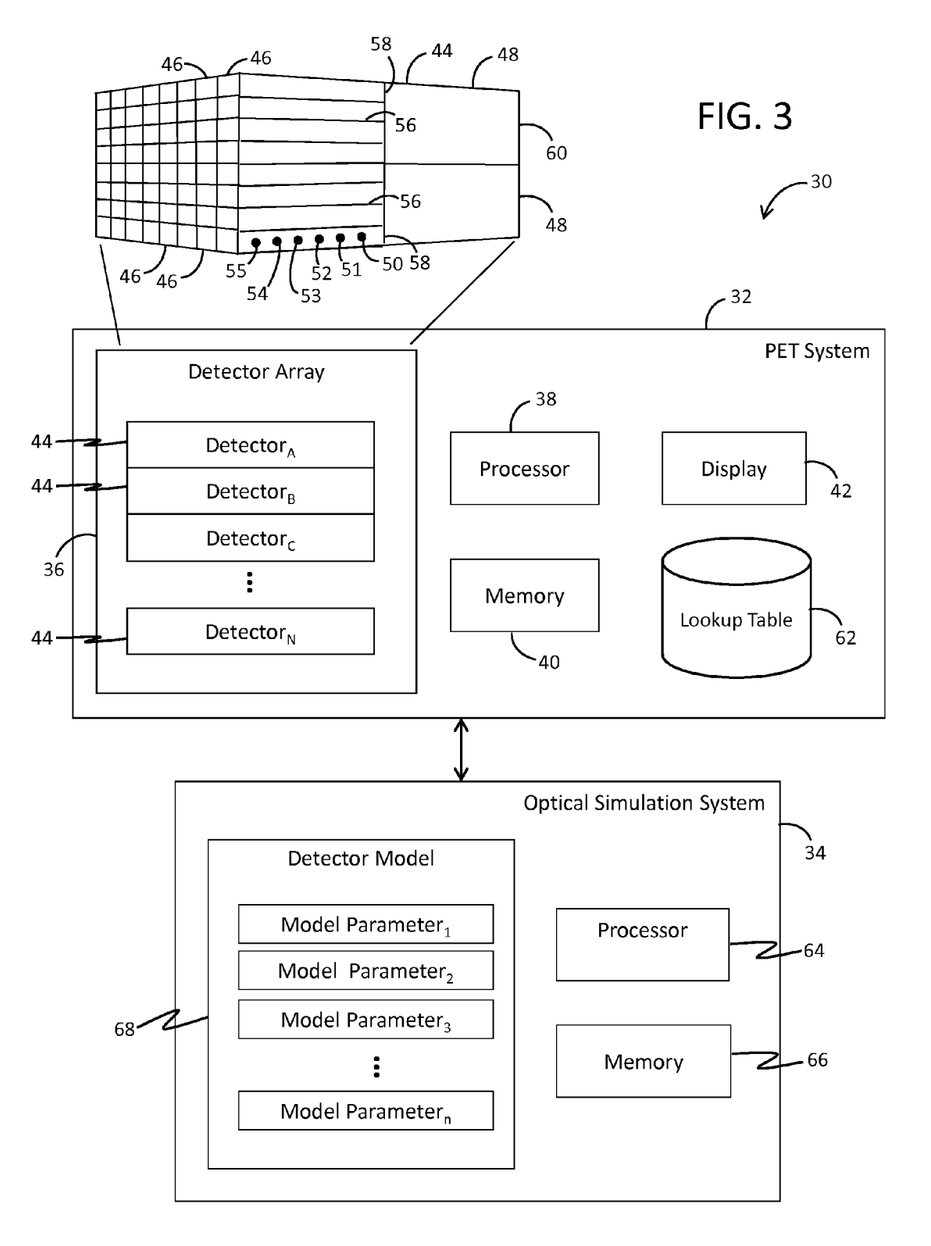
FIG. 3 is a block diagram of a PET system configured to compensate time-of-flight information according to one embodiment and an optical simulation system operable to configure the PET system according to another embodiment.

FIG. 3 shows a system 30 including a PET system 32 and an optical configuration system 34 coupled to, and in communication with, the PET system 32. The PET system 32 is a PET imaging system, but may be or include a computer, workstation, database, server, or other system. The PET system 32 includes an array 36 of detectors (Detector$_A$, Detector$_B$, . . . Detector$_N$), a processor 38, a memory 40, and a display 42. The detector array 36 may be arranged in a ring that surrounds a patient or subject being scanned by the PET system 32. Additional, different, or fewer components may be provided. For example, the PET system 32 may be a computer without the detector array 36 for operating on data acquired by another system. Alternatively or additionally, the system 30 includes magnetic resonance imaging (MRI), computed tomography (CT), or other imaging or scanner components. Other parts of the PET system 32 may include power supplies, communications systems, image processing systems, tomography generation systems, and user interface systems. The PET system 32 may include more than one imaging system or subsystem. Any now known or later developed PET imaging system may be used.

An exemplary PET detector 44 of the PET detector array 36 is shown in greater detail to depict a plurality of scintillation crystals 46 disposed in a grid arrangement adjacent to, and in optical communication with, a set of photodetectors or other optical sensors 48. Each optical sensor 48 may include a photomultiplier tube. A wide variety of other optical sensors may be used in other embodiments. For example, the optical sensors 48 may include avalanche photo diodes (APDs). The scintillation crystals 46 may include one or more bismuth germanium oxide, gadolinium oxyorthosilicate, or lutetium oxyorthosilicate crystals (or crystal regions or components), but other crystal materials may be used. The refractive index and other characteristics of the crystal material(s) may be incorporated into the PET detector model as one or more parameters. The shape and/or dimensions of each scintillation crystal 46 may also be incorporated into the simulation via one or more parameters (e.g., length or depth, lateral width, height, surface finish, etc.). The model may thus determine the correction factors for a specific size scintillation crystal, each of which in this example may be 3 mm×3 mm×20 mm. The shape of the scintillation crystals may vary, and need not have a square cross-section or other rectilinear shape.

Each scintillation crystal 46 may be configured in a manner that allows the depth of interaction to be captured. In some examples, the scintillation crystal 46 includes multiple layers or regions (e.g., pixelated scintillators). The layers or regions may have varying material types across the depth or width of the PET detector 44 to generate an indication of the depth of interaction. For example, different scintillators (or scintillator layers) may develop unique or different pulse shapes. One layer may generate a shorter (faster) decaying pulse, while another layer generates a longer (slower) decaying pulse. The gamma interaction position may thus be estimated through pulse shape analysis. Alternatively or additionally, the reflector interfaces between the scintillation crystals 46 may be configured such that the sharing of light between the scintillation crystals varies over the depth of the scintillation crystals. For example, in certain reflector arrangements, a significant amount of light may be shared when the light is generated at shallow depths (e.g., near the front face of the crystal), with less light being shared when the interaction occurs as the depth approaches a rear face of the crystal. In other examples, each PET detector 44 may include optical sensors at both ends of the scintillation crystal, from which the signals may be compared (e.g., a ratio comparison) to determine the depth of interaction. The manner in which the depth of interaction information is obtained may vary. The disclosed systems and methods may use any now or hereafter developed technique to determine the depth of interaction.

The optical sensors 48 are configured to capture visible photons generated in the scintillation crystals 46 at a depth of interaction within the scintillation crystals 46 as a result of interaction with a gamma photon emitted from an event in the patient. The PET detector 44 may be oriented such that the gamma photon passes through the optical sensors 48 before reaching the scintillation crystals 46, although the orientation may vary from the example shown. One or more parameters of the simulation model may reflect the orientation of the PET detector 44. For example, the thickness (or depth) of the optical sensors may be incorporated into the simulation model. The optical sensors 48 may have a coating material (e.g., glass, epoxy, etc.) and other physical components (including, for instance, a silicon body of the sensor itself) having properties affecting travel. The type and thickness of the optical sensors 48 may also be incorporated into the simulation model because the possibility of additional reflections (and further time dispersion) may increase with increasing sensor thickness.

The interaction may occur at any position within the scintillation crystal 46. Examples of a plurality of interaction depths 50-55 are shown to illustrate the difference between a shallow depth of interaction near the optical sensors 48 (e.g., the interaction depth 50) and a deep depth of interaction distal the optical sensors 48 (e.g., the interaction depth 55).

Each scintillation crystal 46 may be separated from adjacent crystals by a reflective surface 56 or other reflector, or both. For example, the reflective surface 56 may be formed via a surface finishing process. The characteristics of the reflective surface 56 or other reflector may be incorporated into the simulation model. For example, one or more parameters of the simulation model may be indicative of the arrangement of reflectors within the PET detector 44. In this example, the PET detector 44 has a grid arrangement of reflectors that corresponds with the shape and size of the respective scintillation crystals 46. In other examples, the reflector arrangement may deviate from the scintillation crystal arrangement.

Other surfaces of the scintillation crystals 46 may also be incorporated into the simulation model. The scintillation crystals 46 may have an end surface 58 proximate the optical sensors 48 configured with a cover, coupling film, or other material. Alternatively or additionally, the optical sensors 48 may have a coupling film or mounting material adjacent the scintillation crystals 46. In some embodiments (e.g., two sensor embodiments), the optical sensors 48 may have a sensor cover 60 on an exposed or outer face through which the gamma photons travel before interaction with the scintillation crystal 46. Parameters of the simulation model may be indicative of the thickness, material type, and other characteristics of one or more of these surfaces, covers, films, or materials.

The arrangement of the optical sensors 48 may also be incorporated into the simulation model. In one example, the PET detector 44 has four optical sensors 48 arranged in a two-by-two grid. The number, size, and other aspects of the arrangement of the optical sensors 48 relative to the scintillation crystals 46 may vary from the example shown, representations of which may be incorporated into the model. Additional or fewer optical sensors, in various arrangements, may be used.

The configuration of the detector array 36 may vary from the example shown. The PET detectors 44 may be arranged individually or in any group configuration. Each PET detector 44 may generate three analog signals, two position signals and one energy signal. Other output formats may be provided. To detect positron emission events and the gamma photons arising therefrom, the PET detector array 36 may be positioned to substantially surround a portion of a patient.

Further details regarding an exemplary PET detector configurations and components suitable for use with the disclosed methods and systems are set forth in U.S. Patent Publication No. 2011/0192982 ("System and Method for Providing Depth of Interaction Detection Using Positron Emission Tomography"), the entire disclosure of which is hereby incorporated by reference.

In operation, the signals from the PET detector array 44 are processed to identify specific events. The timing and location information are used to determine the existence of a valid event (e.g., positron emission with gamma photon pair) and the location of the event (e.g., line along which the event occurred). The detected events or emission information is stored in the memory 40. The timing information includes time-of-flight information. Further details regarding the use and processing of such information of the PET system 32 to reconstruct images are set forth below in connection with FIG. 4.

The PET system 32 includes a data store or other memory 62 in which time-of-flight correction data is stored. The time-of-flight correction data is indicative of the timing offset data generated via the above-described simulation based on an optical simulation model of the PET detector 44. The correction data may include a correction factor, such as a timing adjustment or correction time, for a number of depths of interaction. In one example, the data store 62 is configured as a lookup table of correction factors as a function of depth of interaction. Alternatively or additionally, the data store 62 may provide correction data representative of a curve or function that may be used by the processor 38 to generate a correction factor for a given depth of interaction. Thus, the data store 62 need not be configured as a database as shown. The configuration, format, and other characteristics of the data store 62 may vary, and may be integrated with the memory 40 to any desired extent. The processor 38 is in communication with the data store 62 and the PET detectors 44 of the detector array 36 to compensate the time-of-flight data based on the correction data and the depth of interaction in the PET detector 44 (e.g., depth within the scintillation crystals 46).

The correction factors or other correction data may be provided to the PET system 32 by the optical simulation system 34. The PET system 32 and the optical simulation system 34 may be coupled to, or in communication with, one another, or be integrated to any desired extent. In the example shown in FIG. 3, the optical simulation system 34 includes a processor 64 and a memory 66 coupled to, or in communication with, the processor 64. In other examples, the PET system 32 and the optical simulation system 34 share one or more processors, and/or share one or more memories.

The memory 66 may be configured to store data representative of an optical simulation model 68 of the PET detector 44. The data representative of the optical simulation model 68 may include information indicative of a number of model parameters (1-n), as described above. The memory 66 may include further data indicative of code or instruction sets to be implemented by the processor 64 to generate the correction factors or other correction data. The code or instructions sets may include code or instructions for implementing one or more of the optical simulators described above.

Each memory 40, 66 or data store 62 is a buffer, cache, RAM, removable media, hard drive, magnetic, optical, database, or other now known or later developed memory. Each memory 40, 66 or data store 62 is a single device or group of multiple devices. Each memory 40, 66 or data store 62 is shown within the PET system 32 or the optical simulation system 34, but may be outside or remote from other components of the PET system 32 or the optical simulation system 34, such as a database or PACS memory.

Each memory 40, 66 or data store 62 may store data at different stages of processing. For example, the memory 40 may store raw data representing detected events without further processing, filtered or thresholded data prior to reconstruction, reconstructed data, filtered reconstruction data, an image to be displayed, an already displayed image, or other data. Each memory 40, 66 or data store 62 (or a different memory) may store data used for processing, such as storing the data after one or more iterations and prior to a final iteration in reconstruction. For processing, the data bypasses the memory 40, 66, is temporarily stored in the memory 40, 66, or is loaded from the memory 40, 66.

Each memory 40, 66 is additionally or alternatively a non-transitory computer readable storage medium storing processing instructions. For example, the memory 40 stores data representing instructions executable by the programmed processor 38 for reconstructing a positron emission tomography image for dynamic study and/or reconstructing an image in emission tomography. As another example, the memory 66 stores data representing instructions executable by the programmed processor 64 for optically simulating the detectors as a function of depth of interaction. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software stored or otherwise embodied on a computer-readable memory, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

Each processor 38, 64 is a general processor, digital signal processor, graphics processing unit, application specific integrated circuit, field programmable gate array, digital circuit, analog circuit, combinations thereof, or other now known or later developed device for processing emission information. Each processor 38, 64 is a single device, a plurality of devices, or a network. For more than one device, parallel or sequential division of processing may be used. Different devices making up each processor 38, 64 may perform different functions, such as one processor for filtering and/or subtracting raw data or reconstructed images. Each processor 38, 64 may include an application specific integrated circuit or field programmable gate array for performing various operations, such as iterative reconstruction. In one embodiment, the processor 38 is a control processor or other processor of a PET imaging system. The processor 64 is a processor of a computer or workstation.

Each processor 38, 64 operates pursuant to stored instructions to perform various acts described herein. For example, the processor 38 may be operable to process data indicative of detected events, correct time-of-flight, and implement iterative reconstructions from different collections of data. As another example, the processor 64 simulates correction values for a given detector or PET system, or for a type of detector or PET system. Each processor 38, 64 may be configured by code or instructions sets stored on a memory, by firmware, and/or by hardware to perform any or all of the acts described herein.

The display 42 is a CRT, LCD, plasma screen, projector, printer, or other output device for showing images generated by the PET system 32. The display 42 may be used to display a user interface for controlling the PET system 32 and/or the optical simulation system 34. The optical simulation system 34 may have a separate display or user interface for control thereof.

Figure 4:
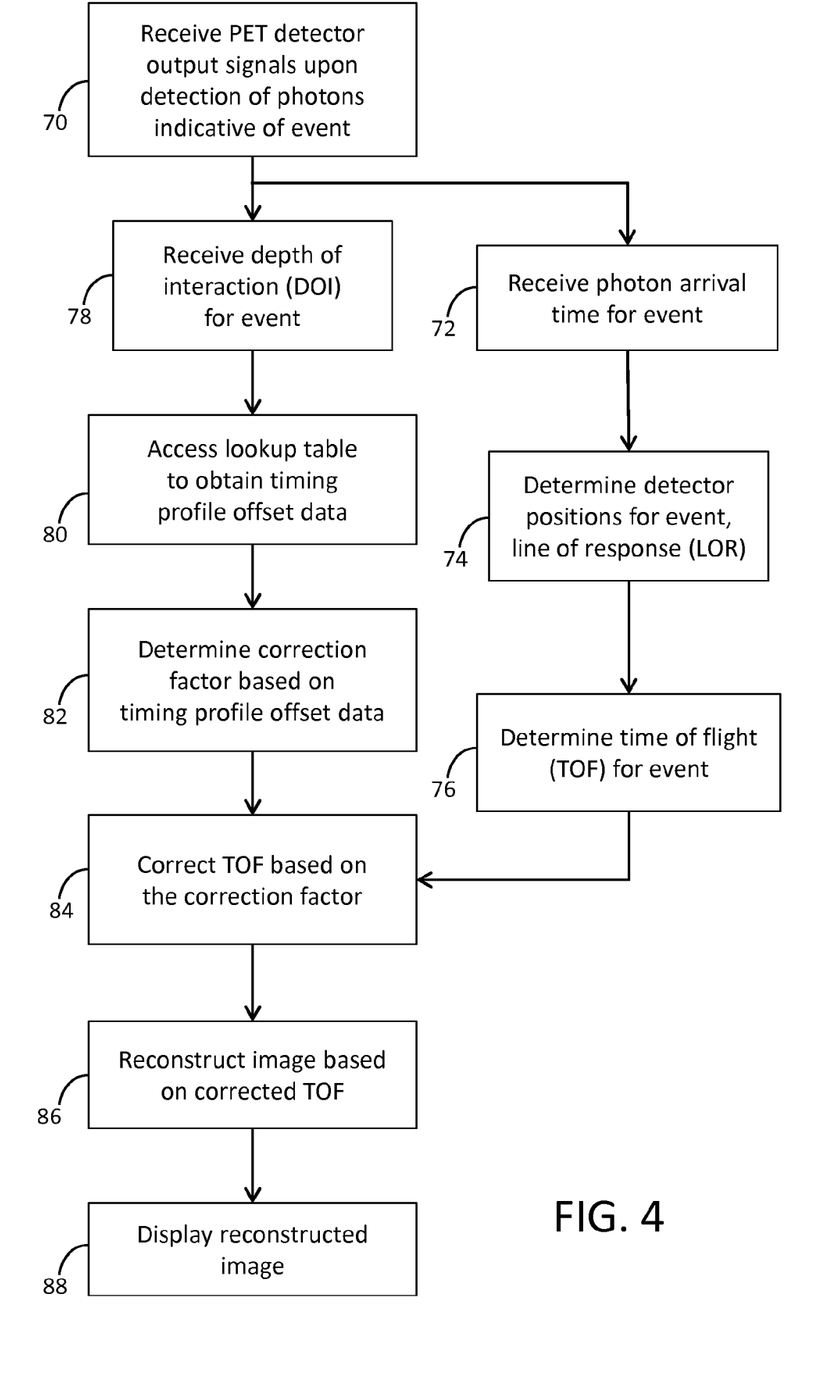
FIG. 4 is a flow diagram of one embodiment of a method for reconstructing an image in time-of-flight PET based on depth of interaction (DOI) corrected time-of-flight data.

FIG. 4 depicts one example of a PET imaging method that may be implemented by the PET system 32 or other system configured in accordance with the methods and systems disclosed herein. The method may begin with the detection in act 70 of gamma photons by two or more of the PET detectors of the PET system indicative of one or more events in a patient or subject. The output signals of such PET detectors reflect the detection of the visible photons generated from the interaction of the gamma photons with scintillation crystals of the PET detectors. The output of the PET detectors is received in act 70. The output signals may be processed to identify the PET detectors that detected gamma photons. Information regarding the arrival times of the visible photons in each PET detector may also be received in act 70 or in a separate act 72 as shown. Analog constant fraction discriminators (CFD) may be used to determine timing information for the PET detectors. Other devices or techniques may be used to determine the arrival time information. The arrival time information is used in act 74 to determine a pair of the PET detectors associated with the same event and, thus, disposed along a line of response (LOR). The pair of PET detectors are paired based on a matching, comparison, or other processing of the arrival times of the visible photons. The arrival time information is also used to determine in act 76 respective times of flight for the gamma photons detected by the pair of PET detectors. The manner in which the time-of-flight data is generated may include any processing techniques and devices.

The visible photons are generated at respective depths of interaction within the pair of PET detectors as described above. Information indicative of the depths of interaction (DOI) is received in act 78. The receipt of the DOI information may occur before, during, or after the implementation of one or more of the acts 72, 74, 76. Subsequent processing of the DOI information may also occur in parallel with, before, or after implementation of one or more of the acts 72, 74, 76. The order of implementation for these processing steps may vary between serial, parallel, iterative, batch, and/or other modes of operation as the PET system acquires and processes information regarding a number of events.

In the example of FIG. 4, a lookup table is accessed in act 80 to obtain data indicative of a timing profile offset. The lookup table may include a list of correction factors, such as offset times, for a number of depths of interaction. The offset times or other correction factors are based on the optical simulation data generated as described herein. The DOI information may be used as an index to the list or other arrangement of correction factors in the lookup table. A correction factor for the depth of interaction is determined in act 82 based on the timing profile offset data. In one embodiment, the correction factor for the depth of interaction closest to the depth indicated by the DOI information is selected. Alternatively, a correction factor is determined from an extrapolation or interpolation (e.g., linear) of the closest correction factors. Other methods may be used to determine the correction factor, including, for instance, procedures that include fitting a curve or other function to the correction factor data retrieved from the lookup table, and then using the curve or other function to determine the correction factor. In still other examples, data indicative of a curve or function is accessed in act 80 from which timing offset values may be generated.

In act 84, the time-of-flight data for the gamma interaction is corrected. The time-of-flight data may include the data for a respective pair of gamma interactions. The correction includes adjusting the time-of-flight data based on the correction factor, which, in turn, is based on the DOI information and simulation-based timing offset data. The time-of-flight data for each PET detector may be adjusted in accordance with the timing offset by, for instance, shifting the arrival times in accordance with the timing offset.

After data for one or more events has been collected and processed, the imaging method may proceed to implement an image reconstruction procedure in act 86. Alternatively, one or more modules of the image reconstruction procedure may be implemented before or during one or more of the above-described acts. The image reconstruction procedure is configured to improve the image resolution via use of the corrected time-of-flight information. Display of the reconstructed image may then occur in act 88.

The DOI information may be available and obtained by the PET system for one or more other purposes. For example, the DOI information may be used to improve spatial resolution in, for instance, small animal subjects. Thus, in some cases, the DOI information may be used in connection with determining the line of response.

Figure 5:
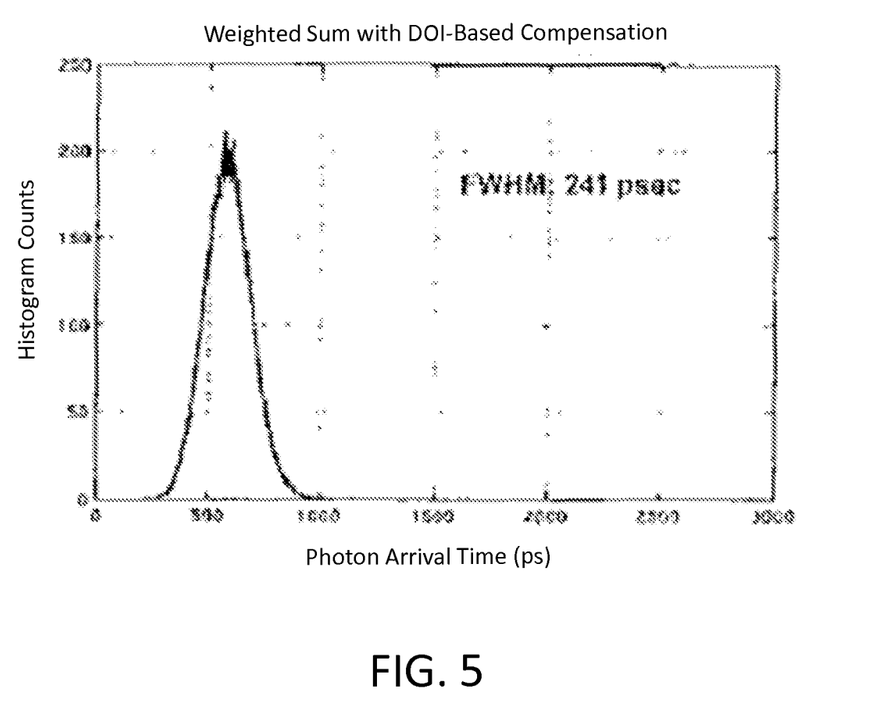
FIG. 5 is a graphical plot of photon arrival times after DOI-based compensation in accordance with one embodiment.

FIG. 5 depicts a histogram of data representative of adjusted photon arrival times for a number of different depths of interaction. The photon arrival times have been adjusted in accordance with one embodiment of the disclosed methods and systems. Each photon arrival time is shifted in accordance with a timing offset based on the depth of interaction for the gamma photon. The histogram depicts the number, or count, of photon arrivals over a range of arrival times shown. While the arrival times remain distributed over a range, the distribution is less dispersed due to the time shifts occurring via the compensation. In one example, the full width at half maximum (FWHM) characteristic of the arrival time plot decreased from 271 ps to 241 ps.

The data shown in FIG. 5 reflects further optical simulation of a PET detector. The optical simulation may use the same model relied upon to determine the timing offsets or other the correction factors. The histogram counts are weighted to reflect the higher likelihood of interaction with decreasing depths of interaction.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method of configuring a positron emission tomography (PET) system, the method comprising:
    simulating, with a processor, photon travel within a detector of the PET system via an optical simulation model of the detector;
    generating, via the simulating, a photon timing profile for a plurality of depth of interaction (DOI) positions within the detector;
    determining a time-of-flight correction factor for each DOI position of the plurality of DOI positions based on the simulated photon travel, the correction factor being indicative of a respective time offset of each photon timing profile; and
    configuring the PET system to determine time-of-flight values in accordance with the time-of-flight correction factors.

2. The method of claim 1 wherein the optical simulation model is configured in accordance with geometric characteristics of a scintillation crystal of the detector.

3. The method of claim 1 wherein the optical simulation model is configured in accordance with a characteristic of a surface of a scintillation crystal of the detector.

4. The method of claim 1 wherein the optical simulation model is configured in accordance with a characteristic of an optical sensor of the detector.

5. The method of claim 4 wherein the characteristic of the optical sensor is indicative of an optical sensor arrangement of the detector.

6. The method of claim 1 wherein the optical simulation model is configured in accordance with a characteristic of a reflector arrangement of the detector.

7. The method of claim 1 further comprising configuring an optical simulator in accordance with a set of parameters of the optical simulation model, each parameter being indicative of a characteristic of the detector affecting the photon travel within the detector, wherein simulating the photon travel within the detector comprises simulating operation of the detector using the configured optical simulator.

8. The method of claim 1 wherein determining the time-of-flight correction factor comprises comparing the photon timing profile with a baseline photon timing profile.

9. The method of claim 8 wherein comparing the photon timing profile comprises determining a time difference between the photon timing profile and the baseline photon timing profile.

10. The method of claim 9 wherein the time difference is based on respective profile center points of the photon timing profile and the baseline photon timing profile.

11. The method of claim 1 wherein configuring the PET system comprises storing the time-of-flight correction factors in a memory coupled to a processor of the PET system.

12. A positron emission tomography (PET) system comprising:
- a detector comprising a scintillation crystal and an optical sensor in optical communication with the scintillation crystal, the optical sensor being configured to capture photons generated in the scintillation crystal at a plurality of depths of interaction;
- a memory in which time-of-flight correction data is stored, the time-of-flight correction data being indicative of timing offset simulation data based on an optical simulation model, the optical simulation model being configured in accordance with a set of parameters to simulate photon travel within the detector from each depth of interaction of the plurality of depths of interaction, the set of parameters comprising a first parameter representative of the scintillation crystal; and
- a processor in communication with the memory and the detector to compensate time-of-flight data based on interaction depth data and the time-of-flight correction data.

13. The PET system of claim 12, wherein the first parameter comprises a geometrical parameter configured to model the scintillation crystal.

14. The PET system of claim 12 wherein the first parameter comprises an external surface parameter configured to model the scintillation crystal.

15. The PET system of claim 12 wherein the set of parameters comprises a second parameter representative of a sensor cover of the optical sensor.

16. The PET system of claim 12 wherein the set of parameters comprises a second parameter representative of an optical sensor arrangement of the detector.

17. The PET system of claim 12 wherein the set of parameters comprises a reflector parameter configured to model a reflector arrangement of the detector.

18. A method of positron emission tomography (PET), the method comprising:
- receiving data indicative of a depth of a gamma interaction at which photons are generated for detection by a PET detector;
- correcting, with a processor, a time of flight for the gamma interaction based on the depth and based on timing offset data, the timing offset data being based on a simulation of operation of the PET detector at a plurality of depths of interaction, the simulation being based on an optical model of the PET detector, the optical model being configured in accordance with a plurality of parameters of the PET detector; and
- reconstructing an image based on the corrected time of flight;
- wherein the optical model is configured in accordance with a plurality of parameters representative of a scintillation crystal of the PET detector.

19. The method of claim 18 wherein the optical model is further configured in accordance with a first optical sensor parameter representative of an optical sensor cover of the PET detector, a second optical sensor parameter representative of an optical sensor arrangement of the PET detector, and a reflector parameter representative of a reflector arrangement of the PET detector.

20. The method of claim 18, further comprising displaying the reconstructed image.

* * * * *